(12) United States Patent
Nagai et al.

(10) Patent No.: US 9,877,368 B2
(45) Date of Patent: Jan. 23, 2018

(54) OPTICAL ANALYZER

(71) Applicant: SHIMADZU CORPORATION, Kyoto-shi, Kyoto (JP)

(72) Inventors: Yusuke Nagai, Kyoto (JP); Keisuke Ogawa, Kyoto (JP); Masato Watanabe, Kyoto (JP); Kumiko Jingu, Kyoto (JP); Masanori Fujiwara, Kyoto (JP); Tomoyuki Yamazaki, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 73 days.

(21) Appl. No.: 15/015,810

(22) Filed: Feb. 4, 2016

(65) Prior Publication Data

US 2016/0234904 A1    Aug. 11, 2016

(30) Foreign Application Priority Data

Feb. 9, 2015    (JP) .................................. 2015-023173

(51) Int. Cl.
*H05B 33/08*    (2006.01)
*G01N 21/33*    (2006.01)

(52) U.S. Cl.
CPC ......... *H05B 33/0851* (2013.01); *G01N 21/33* (2013.01); *G01N 2201/0621* (2013.01);
(Continued)

(58) Field of Classification Search
CPC ............ H05B 33/0851; H05B 33/0884; G01N 21/33; G01N 2201/0621; G01N 2201/063;
(Continued)

(56) References Cited

U.S. PATENT DOCUMENTS 5,037,199 A * 8/1991 Hlousek ............... G01N 21/255
356/246
5,151,628 A * 9/1992 Osawa ............... A61B 5/02416
250/205

(Continued)

FOREIGN PATENT DOCUMENTS

JP    2011-237384 A    11/2011

*Primary Examiner* — John Lee
(74) *Attorney, Agent, or Firm* — Sughrue Mion, PLLC

(57) ABSTRACT

Provided is an optical analyzer for performing a feedback control on the amount of light emitted from an LED as a light source, in which the configuration of an optical system is made simple and the degree of freedom in optical system arrangement is secured. An optical member 2 for focusing most of light while discharging part of the light as unfocused light is provided on an optical path from a light casting unit 1 to a sample cell 3. The optical member 2 can be achieved with a simple configuration, for example, two ball lenses spaced apart by a predetermined distance from each other. The light focused by the optical member 2 is cast as measurement light into the sample cell 3. Meanwhile, a second photodetector 5 is arranged at a position where the unfocused light reaches. The second photodetector 5 generates a detection signal in accordance with the amount of light that has entered the second photodetector 5 as monitored light, and a drive current to be supplied to an LED is controlled through a drive current controlling unit 6 and a current source 7 such that the amount of light is maintained at a fixed level.

3 Claims, 1 Drawing Sheet

(52) U.S. Cl.
CPC ............... *G01N 2201/0638* (2013.01); *G01N 2201/0692* (2013.01); *G01N 2201/0695* (2013.01)

(58) Field of Classification Search
CPC ... G01N 2201/0638; G01N 2201/0639; G01N 2201/0634; G01N 2201/0624; G01N 2201/0692; G01N 2201/0695; G01N 21/255
USPC ........................................................ 250/205
See application file for complete search history.

(56) References Cited

U.S. PATENT DOCUMENTS

| | | | | |
|---|---|---|---|---|
| 5,250,797 | A * | 10/1993 | Sano | G03F 7/70058 250/205 |
| 5,589,935 | A * | 12/1996 | Biard | A47L 15/4297 134/113 |
| 5,659,414 | A * | 8/1997 | Appel | G02B 26/123 250/205 |
| 5,786,890 | A * | 7/1998 | Noh | G11B 7/124 250/205 |
| 6,107,620 | A * | 8/2000 | Shiba | G06K 15/1214 250/205 |
| 6,266,314 | B1 * | 7/2001 | Fukakusa | G11B 7/127 369/112.01 |
| 6,303,916 | B1 * | 10/2001 | Gladnick | H05B 41/3922 250/205 |
| 6,527,460 | B2 * | 3/2003 | Cohen | G02B 6/4214 250/205 |
| 7,045,752 | B2 * | 5/2006 | Posamentier | G01J 1/4257 250/205 |
| 7,473,879 | B2 * | 1/2009 | Ng | F21K 9/00 250/205 |
| 8,901,478 | B2 * | 12/2014 | Hung | G01J 1/0407 250/205 |
| 9,304,280 | B2 * | 4/2016 | Gulari | G02B 7/027 |
| 2001/0028484 | A1 * | 10/2001 | Sasaki | G02B 5/32 359/19 |
| 2004/0084605 | A1 * | 5/2004 | Yokoyama | H04N 1/0286 250/205 |
| 2008/0018894 | A1 * | 1/2008 | Zu | G01N 15/1459 356/338 |
| 2012/0104225 | A1 * | 5/2012 | McEldowney | G01J 1/0228 250/205 |
| 2012/0193513 | A1 * | 8/2012 | Widzgowski | G02B 21/06 250/205 |
| 2015/0090900 | A1 * | 4/2015 | Banks | G01N 21/645 250/432 R |
| 2015/0136945 | A1 * | 5/2015 | Babic | G02B 27/108 250/205 |
| 2016/0187250 | A1 * | 6/2016 | Nagai | G01N 21/255 356/436 |
| 2016/0234904 | A1 * | 8/2016 | Nagai | H05B 33/0851 |
| 2016/0313248 | A1 * | 10/2016 | Nagai | G01N 21/645 |

* cited by examiner

OPTICAL ANALYZER

TECHNICAL FIELD

The present invention relates to an optical analyzer for casting light into or onto a sample and detecting transmitted light, reflected light, scattered light, fluorescent light, and other forms of light obtained from the sample in response to the cast light.

BACKGROUND ART

In a measurement of an absorbance of a liquid sample or gas sample, an optical analyzer is normally used, such as an ultraviolet-visible spectrophotometer or photodiode array detector. For example, an ultraviolet-visible spectrophotometer commonly includes a deuterium discharge tube as a light source for the ultraviolet wavelength region and a halogen lamp as a light source for the visible wavelength region. In recent years, an ultraviolet-visible spectrophotometer including, as a light source, a xenon flash lamp having a longer life than those of the halogen lamp and deuterium discharge tube has also been developed. In any case, optical analyzers including those light sources are normally configured such that monochromatic light is extracted by a monochromator including a diffraction grating or similar device and cast into or onto a sample, or such that light obtained from a sample is introduced into a light-dispersing device and dispersed into wavelength components, which are then partially or entirely introduced into and detected by a detector.

In recent years, with the advancement and rapid spread of the light emitting diode (LED) technology, LEDs have also been increasingly used as light sources in optical analyzers. Since LEDs have a comparatively narrow peak in their emission spectra, they are less suitable for applications that require the scan of a wide range of wavelengths. However, LEDs are suited to optical analyzers that cast light having a specific wavelength into or onto a sample, as in the case of an absorptiometer and fluorometer. LEDs are not only far more inexpensive than the above-mentioned light sources, but also have a long life and operate with high reliability. On the other hand, in general, the amount of light emitted from an LED considerably fluctuates with an ambient temperature change. In optical analyzers, such a fluctuation in the amount of light makes the measurement result less accurate. Therefore, a feedback control that adjusts the drive current to the LED so as to maintain the amount of light at a fixed level has been known up to now as one of the methods for reducing such an influence of the temperature dependency of the amount of light.

For example, in an apparatus described in Patent Literature 1, a slit component is provided between a sample and a lens for focusing light emitted from an LED, and a monitoring photodetector is attached to the slit component. The monitoring photodetector detects light that does not pass through an opening of the slit component, that is, is not used as measurement light, of the light that is focused by the lens and is applied to the slit component. Then, a drive current for causing the LED to emit light is controlled such that the amount of monitored light detected by the monitoring photodetector is at a fixed level. According to this configuration, because the light focused by the lens is used as the monitored light, the detection accuracy of the amount of light can be improved, and the amount of light can be made stable by the feedback control.

CITATION LIST

Patent Literature

[Patent Literature 1] JP 2011-237384 A

SUMMARY OF INVENTION

Technical Problem

However, in the case of the apparatus described in Patent Literature 1, because the light that is focused by the lens to be cast into or onto the sample is used as the monitored light, the installation position of the monitoring photodetector is considerably limited, leading to a lower degree of freedom in optical system design. Although the focused light essentially needs to be cast into or onto the sample without being wasted as far as possible and be used as the measurement light, in the apparatus described in Patent Literature 1, part of the light focused by the lens is not used as the measurement light, and this is disadvantageous to improvement in the measurement accuracy of the absorbance of the sample and other properties.

An object of the present invention, which has been made in order to solve the above-mentioned problems, is to provide an optical analyzer for controlling the amount of light emitted from a light source based on a detection result of monitored light detected by a monitoring photodetector, the optical analyzer having a simple configuration and enabling a high degree of freedom in the installation position of the monitoring photodetector and a high degree of freedom in optical system designing.

Solution to Problem

An optical analyzer according to the present invention, which has been made in order to solve the above-mentioned problems, is an optical analyzer for analyzing a target sample by casting light from a light casting unit into or onto the sample and introducing light obtained from the sample in response to the cast light into a photodetector, the light casting unit including a light-emitting semiconductor device as a light source, the optical analyzer including:

a) an optical member for focusing received light on the sample while generating unfocused light without focusing part of the received light, the optical member being arranged on an optical path from the light casting unit to the sample;

b) a second photodetector arranged at a position where the unfocused light generated by the optical member reaches; and c) a controlling unit for controlling a drive current to be supplied to the light-emitting semiconductor device based on an intensity signal generated by the second photodetector such that an amount of light is at a fixed level.

Examples of the light-emitting semiconductor device include light emitting diodes (LED), super luminescence diodes (SLD), and laser diodes (LD), and all of these diodes are light sources that discharge monochromatic light or light that is equivalent to the monochromatic light and has a narrow wavelength band with a comparatively narrow peak width.

In the optical analyzer according to the present invention, the light that is emitted from the light casting unit by supplying the drive current to the light-emitting semiconductor device such as an LED enters the optical member. The optical member includes, for example, a plurality of spherical lenses spaced apart by a predetermined distance from each other. The spherical lenses here include spherical convex lenses and ball lenses. A large portion of the light that has entered the optical member is focused, and the focused light is cast into or onto the sample. Meanwhile, for example, in the light casting unit, light that is emitted from a position off an extended axis of the optical axis of the optical member becomes the unfocused light that is not focused by the optical member, and the unfocused light is discharged in a direction different from that of the focused light. Part of the unfocused light enters the second photodetector as monitored light, and the intensity signal is generated in accordance with the amount of the incident light. The controlling unit controls the drive current to be supplied to the light-emitting semiconductor device based on the intensity signal generated by the second photodetector such that the amount of light coincides with, for example, a target value.

If the ambient temperature of the light-emitting semiconductor device changes or if the temperature of the light-emitting semiconductor device changes with the passage of time from lighting-up due to its own heat generation, the amount of light emitted from the light-emitting semiconductor device changes, even if the drive current is at a fixed level. To deal with this, in the optical analyzer according to the present invention, a feedback control is performed on the drive current such that the amount of light is at a fixed level, and hence the amount of light cast into or onto the sample is maintained at a substantially fixed level regardless of the temperature.

In this case, because a light portion that enters the second photodetector is extremely small in the entire emitted light, the incident light may be feeble, while a temporal fluctuation in the amount of light with a temperature change is significantly slow, and hence the feedback control can be performed at low speed. Accordingly, the light reception time (charge accumulation time) can be set to be long in the second photodetector, whereby the smallness of the amount of incident light can be compensated. Moreover, a device having a low operation speed but having a large light receiving area may be used as the second photodetector, or a plurality of photoelectric conversion devices may be connected in parallel as the second photodetector, whereby the smallness of the amount of light per unit area may be compensated.

Advantageous Effects of Invention

With the optical analyzer according to the present invention, a fluctuation in the amount of light emitted from the light source with a temperature change can be suppressed, and the measurement accuracy can be secured. Moreover, in the optical analyzer according to the present invention, the unfocused light is discharged by the optical member in a wide direction, and the discharge direction of the unfocused light can be adjusted by the configuration and arrangement of the optical member. Accordingly, the second photodetector for detecting the monitored light can be arranged with a high degree of freedom. Moreover, for example, it is sufficient to arrange, as the optical member, two ball lenses away by a predetermined distance from each other, and hence the configuration itself of the optical member can be simple. As a result, the optical analyzer can be obtained with a simple configuration and a high degree of freedom in optical system designing.

DESCRIPTION OF EMBODIMENTS

An embodiment of an optical analyzer according to the present invention is hereinafter described with reference to the attached drawings.

Figure 1:
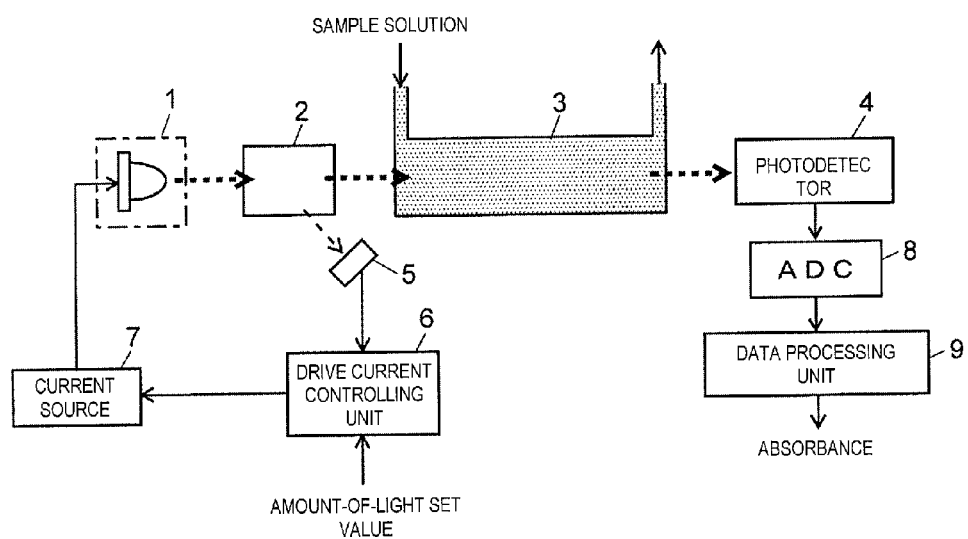
FIG. 1 is a schematic configuration diagram of an absorptiometer as an embodiment of an optical analyzer according to the present invention.

FIG. 1 is a schematic configuration diagram of an absorptiometer as an embodiment of the present invention.

Light emitted from a light casting unit 1 is introduced into a focusing/unfocusing optical member 2, and most of the introduced light is focused and cast as measurement light into a sample cell 3 through which a sample solution to be measured is passing. A light source of the light casting unit 1 is, for example, a deep ultraviolet LED. While passing through the sample cell 3, the measurement light undergoes absorption depending on the components, concentration, and other properties of the sample in the sample cell 3. The light after such absorption enters a photodetector 4, and the photodetector 4 generates a detection signal corresponding to the amount of the incident light. The detection signal is converted into digital data by an analog-to-digital converter (ADC) 8, and a data processing unit 9 calculates the absorbance of the sample in the sample cell 3 based on the digital data.

The focusing/unfocusing optical member 2 discharges, as unfocused light, part of the light received from the light casting unit 1 other than the focused light reflected as the measurement light. A second photodetector 5 is arranged at an arbitrary position within the range within which the unfocused light is discharged from the focusing/unfocusing optical member 2. Part of the unfocused light enters the second photodetector 5 as monitored light, and the second photodetector 5 generates a detection signal corresponding to the amount of the incident monitored light. A drive current controlling unit 6 compares the detection signal corresponding to the amount of the incident monitored light with a predetermined amount-of-light set value, and adjusts a drive current generated by a current source 7 such that the difference between the two is zero. Consequently, the drive current to be supplied to the LED of the light casting unit 1 changes, and the amount of light emitted from the LED changes. In other words, in the absorptiometer of the present embodiment, through a feedback control based on the amount of light that is discharged by the focusing/unfocusing optical member 2 without being focused, the amount of light emitted from the LED is controlled so as to be at a substantially fixed level.

Figure 2:
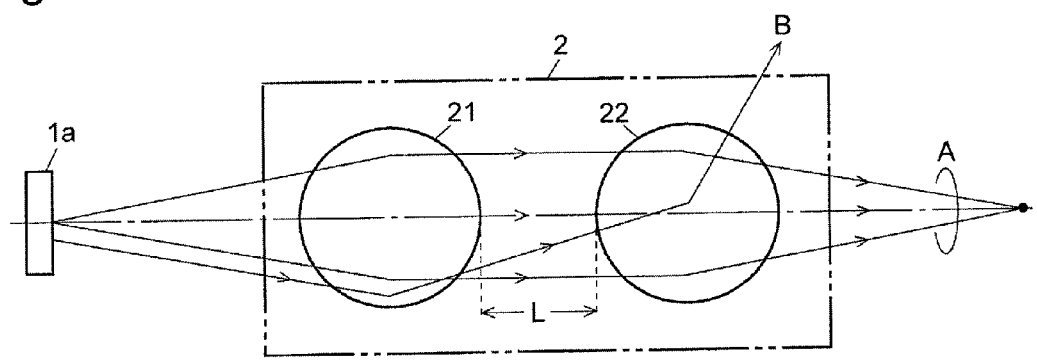
FIG. 2 is a diagram illustrating an example of a focusing/unfocusing optical member in the absorptiometer of the present embodiment.

FIG. 2 is a diagram illustrating an example of the focusing/unfocusing optical member 2.

In this example, in the focusing/unfocusing optical member 2, two ball lenses 21 and 22 having the same diameter are spaced apart by a distance L from each other. A line connecting the central points of the two ball lenses 21 and 22 is defined as an optical axis, and the positional relation between the light casting unit 1 and the focusing/unfocusing optical member 2 is defined such that an LED chip (light emitting part) 1a of the light casting unit 1 is located on an extended line of the optical axis. Light that is emitted from the center (a position on the extended line of the optical axis) of the LED chip 1a while radially spreading is refracted into a substantially parallel light flux by the front-stage ball lens 21, and is refracted and focused by the rear-stage ball lens 22. The resultant light is cast as focused light A into the sample cell 3 (not illustrated).

As illustrated in FIG. 2, light emitted from a position off the center of the LED chip 1a is refracted by each of the two ball lenses 21 and 22, and is discharged as unfocused light B. The unfocused light B is discharged in various directions, and the discharge direction and discharge angle of the unfocused light B depend on the size of the LED chip 1a, the sizes of the ball lenses 21 and 22, the separation distance L between the ball lenses 21 and 22, the distance between the LED chip 1a and the ball lens 21, and other factors. Accordingly, the configuration of the focusing/unfocusing optical member 2 (the sizes of the ball lenses 21 and 22 and the separation distance L between the ball lenses 21 and 22), the separation distance between the focusing/unfocusing optical member 2 and the LED, and other designs may be determined in accordance with a desired installation position of the second photodetector 5. Conversely, the configuration of the focusing/unfocusing optical member 2, the distance between the focusing/unfocusing optical member 2 and the LED, and other designs may be first determined, and the installation position of the second photodetector 5 may be then determined. In any case, the installation position of the second photodetector 5 can be determined independently of at least the discharge direction of the focused light from the focusing/unfocusing optical member 2, so that the degree of freedom in optical system designing is high.

Of course, the focusing/unfocusing optical member 2 is not limited to the configuration illustrated in FIG. 2. For example, two (or more) spherical convex lenses may be used instead of the ball lenses. Alternatively, if an aspherical lens is used, both focused light and unfocused light can be generated by one lens.

In the absorptiometer of the present embodiment, a light portion that enters the second photodetector 5, of the light emitted from the LED is extremely small, and hence the amount of the incident light is normally small. While a temporal fluctuation in the amount of light emitted from the LED with a temperature change is rather small, and hence the feedback control can be performed on the drive current at low speed. Accordingly, the charge accumulation time may be set to be long in the second photodetector 5, whereby a sufficiently large detection signal can be obtained even if the amount of light is small. As a result, feedback control with high accuracy can be achieved even if the amount of light is small.

In the above-mentioned embodiment, the light emitted from the light casting unit 1 is cast as the measurement light into the sample cell 3 without changing the wavelength band of the light. Although the peak width of the LED used as the light source at this time is comparatively narrow, in order to enhance the monochromaticity of the light emitted from the LED, an optical filter having appropriate transmission characteristics may be arranged at any position on the optical path from the light casting unit 1 to the sample cell 3, and, for example, measurement light from which light having a specific wavelength or wavelength band is removed may be cast into the sample cell 3. With this configuration, for example, measurement light exhibiting an independent peak with the highest intensity around 280 nm, that is, measurement light having high monochromaticity can be cast into the sample cell 3.

Although the LED is used as the light source in the absorptiometer of the present embodiment, a super luminescence diode (SLD) having a higher luminance, a laser diode (LD) more excellent in monochromaticity, or other such diodes may be used as the light source.

Although the present invention is applied to the absorptiometer in the above-mentioned embodiment, it is obvious that the present invention can also be applied to apparatuses for casting similar measurement light into the sample cell 3 and measuring reflected light, scattered light, fluorescent light, and other forms of light obtained from the sample in the sample cell 3.

It should be noted that the above-mentioned embodiment and its variations are mere examples of the present invention, and any change, modification, or addition to the present invention appropriately made within the spirit of the present invention will naturally fall within the scope of claims of the present application.

REFERENCE SIGNS LIST

1 . . . Light Casting Unit
1a . . . LED Chip
2 . . . Focusing/Unfocusing Optical Member
21, 22 . . . Ball Lens
3 . . . Sample Cell
4 . . . Photodetector
5 . . . Second Photodetector
6 . . . Drive Current Controlling Unit
7 . . . Current Source
8 . . . Analog-to-Digital Converter
9 . . . Data Processing Unit
A . . . Focused Light
B . . . Unfocused Light

The invention claimed is:

1. An optical analyzer for analyzing a sample, the optical analyzer comprising:
   a) a light source driven by a driving current for emitting light from a first light emitting point and a second light emitting point;
   b) an optical unit provided on an optical line from the light source to the sample for producing focused light from light emitted from the first light emitting point, the focused light being focused on the sample, while producing unfocused light from light emitted from the second light emitting point;
   c) a photodetector arranged at a same side of the optical unit as the sample which the unfocused light reaches; and
   d) a controlling unit for controlling the driving current based on an intensity signal generated by the photodetector such that an amount of light emitted from the light source is at a fixed level.

2. The optical analyzer according to claim 1, wherein the optical unit includes a plurality of lenses spaced apart by a predetermined distance from each other.

3. The optical analyzer according to claim 1, wherein the optical unit includes an aspherical lens.

* * * * *